United States Patent [19]

Haines

[11] Patent Number: 4,832,685
[45] Date of Patent: May 23, 1989

[54] FLUID FLOW CONTROL SYSTEM AND CONNECTING FITTING THEREFOR

[75] Inventor: Stephen W. Haines, Santa Ana, Calif.

[73] Assignee: CooperVision, Inc., Palo Alto, Calif.

[21] Appl. No.: 105,978

[22] Filed: Oct. 6, 1987

Related U.S. Application Data

[63] Continuation of Ser. No. 865,360, May 21, 1986, abandoned, which is a continuation of Ser. No. 741,565, Jun. 5, 1985, abandoned.

[51] Int. Cl.$^4$ ............................................. A61M 1/00
[52] U.S. Cl. ...................................................... 604/30
[58] Field of Search ...................... 604/22, 27, 30–35, 604/50, 65–67, 118–120, 147–149

[56] References Cited

U.S. PATENT DOCUMENTS

| 901,545 | 10/1903 | Morrison . | |
|---|---|---|---|
| 2,302,617 | 11/1942 | Little | 285/122 |
| 2,584,206 | 2/1952 | Hodson | 210/164 |
| 3,693,613 | 9/1972 | Kelman | 128/24 A |
| 3,812,855 | 5/1974 | Banko | 604/31 |
| 3,902,495 | 9/1975 | Weiss et al. | 128/276 |
| 4,007,742 | 2/1977 | Banko | 128/230 |
| 4,024,866 | 5/1977 | Wallach | 128/276 |
| 4,163,700 | 1/1979 | Broadwin | 604/22 |
| 4,168,707 | 9/1979 | Douvas et al. | 128/305 |
| 4,333,454 | 6/1982 | Hargest, III | 128/214 |
| 4,395,258 | 7/1983 | Wang et al. | 604/65 |
| 4,493,698 | 1/1985 | Wang et al. | 604/119 |
| 4,496,342 | 1/1985 | Banko | 604/27 |

FOREIGN PATENT DOCUMENTS 387395 1/1965 Switzerland .

OTHER PUBLICATIONS

Patent Cooperation Treaty International Search Report, International Application No. PCT/US86/01186, filed Jun. 2, 1986.

Primary Examiner—Jerome L. Kruter
Attorney, Agent, or Firm—Vorys, Sater, Seymour and Pease

[57] ABSTRACT

A fluid flow control apparatus specially adapted for use with an ultrasonic surgical tool which provides for irrigation of a surgical site and for aspirating fluid from the site comprises a source of irrigation fluid, comprises an irrigation fluid conduit or conducting the irrigation fluid to a surgical site, an aspiration fluid conduit for conducting fluid away from the surgical site, a suction pump connected to the aspiration fluid conduit for aspirating fluid from the surgical site, a pressure-sensitive control system for removing the source of suction from the aspiration conduit when a predetermined value of suction is exceeded, and a valve for controllably admitting irrigation fluid into the aspiration fluid conduit. A check valve in the irrigation conduit prevents a reverse surge when the irrigation fluid is admitted to the aspiration conduit.

42 Claims, 2 Drawing Sheets

４,832,685

FLUID FLOW CONTROL SYSTEM AND CONNECTING FITTING THEREFOR

CROSS-REFERENCE TO RELATED APPLICATION

This application is a continuation of copending application Ser. No. 865,360, filed May 21, 1986 now abandoned, which is a continuation-in-part of application Ser. No. 741,565, filed June 5, 1984, now abandoned.

BACKGROUND OF THE INVENTION

1. Field of the Invention

This invention relates to fluid control systems for surgical irrigation and aspiration and more particularly to fluid control systems for use with an ultrasonic surgical tool which includes means for irrigation of a surgical site and means for aspiration of fluid from the surgical site.

2. Description of the Prior Art

Intraocular surgery, and removal of cataracts in particular, has been greatly aided by the development of surgical instruments which include cutting or fragmenting means combined with means for irrigating the intraocular surgical site and aspirating therefrom the irrigating fluid together with any tissue fragments produced by the surgical procedure. One instrument of this type is disclosed in U.S. Pat. No. 3,589,363, to Banko et al. The surgical instrument therein disclosed comprises a handpiece which holds an elongated ultrasonic surgical tool and contains means for exciting longitudinal ultrasonic vibrations in the tool. The vibrating tool when applied to a tissue such as the crystalline lens of the eye which has developed a cataract is capable of breaking the tissue into small pieces. The tool is provided with means for supplying an irrigating fluid to the surgical site and aspiration means for removing irrigation fluid and fragmented tissue from the surgical site. The aspiration means includes an axial bore through the ultrasonic tool which is connected to a source of suction whereby the tissue fragments are aspirated from the surgical site, together with the irrigation fluid. Because the ultrasonic surgical tool of this patent fragments the excised tissue into very small particles, which are removed with the spent irrigation fluid, the incision in the eyeball need be only large enough to insert the tool and is substantially smaller than the incision required for removing the lens in one piece. However, since the surgical wound in the eyeball is only large enough to insert the ultrasonic surgical tool and irrigation means, the surgical field is practically entirely enclosed, and controlling the flow of irrigation fluid and aspiration fluid is very important. In particular, the suction applied to the aspiration means must be limited to a safe value, to avoid the danger of collapsing the eyeball. The fluid control system disclosed by Banko et al. is operated by the surgeon and comprises an aspiration pump and electrically operated value means for connecting and disconnecting the suction inlet of the pump to the aspiration tubing which conveys fluid away from the surgical field. The valve is controlled by the surgeon by means of a foot switch.

An improved fluid control system is disclosed by Kelman, U.S. Pat. No. 3,693,313. This apparatus addresses the problem of maintaining the proper pressure in the enclosed surgical field even with the occurrence of blockages in the aspiration conduit. A blockage of occlusion may occur, for example, when a piece of fragmented tissue which is larger than the axial bore of the surgical tool is drawn against the entrance to the axial bore in the tool. When such a blockage occurs in the aspiration line, the negative pressure or suction in the aspiration conduit between the surgical site and the vacuum pump increases. If the blockage is then suddenly released either by the mechanical action of the ultrasonic tool or by the increased value of the suction force, there is a tendency for the fluid within the surgical site to rush suddenly into the aspiration conduit with perhaps disastrous consequences. This is an especially important problem in ocular surgery because the total volume of the fluid in the surgical site is smaller than the volume of fluid in the irrigation and aspiration lines. Accordingly, the flow control system of Kelman, U.S. Pat. No. 3,693,613 provides for automatic rapid equalization of the pressure in the aspiration conduit when occlusion is removed. This is accomplished by providing a flow-sensitive transducer in the aspiration conduit which senses the rate of fluid flow and generates an electrical signal which is sent to a controller. Whenever the flow rate increases suddenly, indicating that a blockage has just been cleared, the controller causes a vent valve in the aspiration conduit to open at once, thus relieving the suction and preventing excessive withdrawal of fluid from the surgical site.

The flow control system of Kelman, U.S. Pat. No. 3,693,613 is effective but somewhat complicated. Accordingly, another flow control system for surgical devices of this type was developed by Weiss, et al., U.S. Pat. No. 3,902,495. In this system irrigation fluid is supplied to the surgical site from a source of fluid via an irrigation conduit provided with a pressure relief valve to prevent the irrigation pressure from becoming too high. Similarly, the aspiration conduit is provided with a relief vent valve which opens to the atmosphere at a preset pressure differential, thereby preventing the suction in the aspiration conduit from exceeding a preset value. In this way, the suction in the aspiration line never exceeds a predetermined preset value, and the surgical site is not exposed to excess suction when a blockage is cleared.

Another variation of the method of U.S. Pat. No. 3,693,613 is disclosed in Banko, U.S. Pat. No. 4,496,342. In Banko's apparatus irrigation fluid is supplied to an enclosed surgical site such as the interior of the eye and withdrawn from the surgical site through an aspiration conduit. A flow-sensitive transducer in the aspiration conduit senses the sudden increase in flow rate which occurs when a blockage in the aspiration tube is released and actuates a valve which releases fluid from a second source of fluid into the aspiration line. At the same time, the aspiration pump is shut off until the flow rate has returned approximately to normal. In this way the surge of fluid out of the eye when an aspiration line blockage is released is greatly diminished.

While these flow control systems are effective, they have not addressed the problem of releasing the blockage itself. At best they have limited the suction to a maximum value or sensed the flow surge after the blockage is released and reduced the surge. They have not incorporated the capability of sensing the blockage and then rapidly and positively, under control of the surgeon, equalizing the pressure in the irrigation and aspiration lines for rapid clearing of a blockage.

Hence a need has continued to exist for a fluid control system for a surgical irrigator/aspirator wherein the excess vacuum in the aspiration tubing after a blockage can be controllably and rapidly released.

SUMMARY OF THE INVENTION

An apparatus has now been developed which provides for rapid controllable release of the pressure in the aspiration line when an occlusion of the line occurs. The apparatus of this invention comprises a source of irrigation fluid, irrigation fluid conduit means for conducting the irrigation fluid to a surgical site, aspiration fluid conduit means for conducting fluid away from the surgical site, suction means in fluid communication with the aspiration fluid conduit means for aspirating fluid from the surgical site, pressure-sensitive control means for removing the source of suction from the aspiration conduit when a predetermined value of suction is exceeded, and means for controllably admitting irrigation fluid into the aspiration fluid conduit.

The invention also comprises a special modified T-connection fitting for conveniently connecting the fluid conduits used in the fluid flow control system.

Accordingly, it is an object of the invention to provide an apparatus for irrigation and aspiration of an enclosed surgical site.

A further object is to provide apparatus for controllably releasing blockages in a surgical aspiration conduit.

A further object is to provide apparatus for rapidly releasing suction in the aspiration line of a surgical aspirator.

A further object is to provide apparatus for rapidly equalizing pressure in a surgical irrigation-aspiration system in order to remove occluding matter.

A further object of the invention is to provide a method for controllably clearing blockages in a surgical irrigation-aspiration system by equalizing pressure in the irrigation and aspiration conduits.

A further object is to provide a fluid connecting fixture for conveniently connecting fluid conduits providing irrigation, aspiration, and pressure sensing in a surgical irrigation-aspiration system.

Further objects of the invention will become apparent from the description of the invention which follows.

BRIEF DESCRIPTION OF THE DRAWINGS

The nature and advantages of the invention will be better understood when the detailed description of the invention is considered in conjunction with the drawings provided, wherein.

DETAILED DESCRIPTION OF THE INVENTION AND PREFERRED EMBODIMENTS

Figure 1:
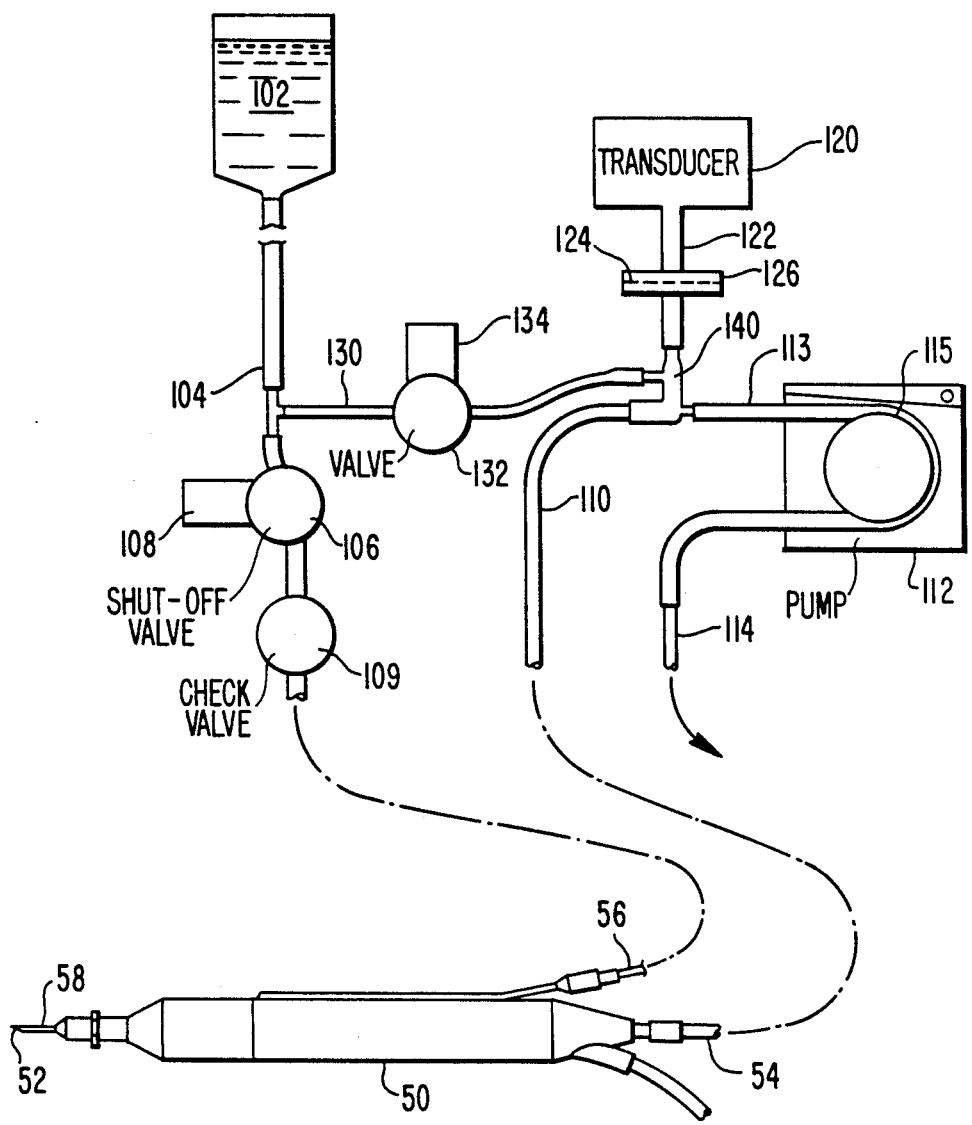
FIG. 1 illustrates schematically a fluid control system for a surgical irrigator/aspirator.

The invention will now be described with reference to a preferred embodiment thereof illustrated in FIG. 1.

The flow control system is illustrated as associated with an ultrasonic surgical handpiece 50 of the type described in U.S. Pat. No. 3,589,363, but it will be understood that the flow control system is adaptable to any surgical irrigation-aspiration system and is of great utility wherever occlusion of the aspiration system can occur. The surgical handpiece 50 is provided with an ultrasonic tool 52 having an axial suction passage connected to an aspiration tube 54. Irrigation fluid is supplied through tube 56 and is directed to the surgical site through a passage coaxial with the ultrasonic tool 52 and defined by sheath 58.

A source of irrigation fluid 102 supplied fluid through irrigation conduit 104 to the irrigation fluid supply tube 56 of the handpiece 50. The source of irrigation fluid 102 may be a conventional bottle or bag of irrigating fluid, e.g., a conventional ophthalmological irrigating fluid for ocular surgery, suspended above the surgical site at an elevation to supply the desired irrigation pressure. This pressure will typically range from 10 mm Hg to 100 mm Hg, preferably 30 mm Hg to 60 mm Hg, for surgical procedures in the anterior chamber of the eye. A shut-off valve 106 is provided in the irrigation conduit to control the starting and stopping of the irrigation. Preferably this shut-off valve 106 is a remotely controllable valve, e.g., an electrically controlled valve operated by a solenoid 108.

The fluid withdrawn from the surgical site through the aspiration tube 54 is drawn through the aspiration conduit 110 of the flow control system by vacuum pump 112 and is discharged through waste conduit 114 to a waste container not shown. The vacuum pump 112 is shown as a peristaltic pump having a pump tube 113 and a rotor 115. Such a pump is preferred in this invention because of its lack of contamination, its good controllability, its relatively high suction capability, and the ease with which the pump may be stopped without special provision for avoiding backflow. However, any appropriate source of vacuum may be used, with the understanding that the control means for disconnecting the source of vacuum from the aspiration line, discussed more fully below, will have to be adapted to the needs of each type of pumps. For example, while a peristaltic type pump may be stopped by simply turning off its drive motor and thereupon inherently prevents backflow, other types of pump may require auxiliary valves to disconnect the source of suction from the aspiration conduit.

According to the method for eliminating occlusions of this invention, the source of vacuum is immediately stopped or disconnected from the aspiration conduit 110 as soon as the vacuum exceeds a predetermined level, which indicates that an occlusion of the aspiration bore in the ultrasonic tool 52 has occurred. For this purpose a pressure sensitive transducer 120 is arranged in fluid transmissive contact with the aspiration conduit 110. Ordinarily the transducer will be connected to the aspiration conduit 110 by a short length of tubing 122 connected to the aspiration conduit 110 by means of a special connecting fitting 140. A hydrophilic-hydrophobic filter 124 mounted in a filter holder 126 is inserted between the aspiration conduit 110 and the transducer connecting tubing 122 in order to protect the transducer from contamination by contact with tissue particles and the like carried along with the aspiration fluid.

The pressure sensitive transducer 120 generates an electrical signal proportional to the vacuum in the aspiration conduit 110 induced by the pump 112. This signal is used to control the pump 112, so that the source of vacuum for the aspiration conduit 110 is quickly removed when the vacuum exceeds the predetermined value, thereby indicating that an occlusion has occured. In its simplest form, the pressure-sensitive transducer 120 may be a simple pressure switch which turns off the motor (not shown) of the peristaltic pump 112. When a peristaltic pump is used it is only necessary to turn off the drive motor to stop the pump, maintain the suction vacuum at the level it had reached, and prevent backflow of waste irrigation fluid. It will be recognized that it is also possible to use a continuously running pump with a controllable shut-off valve between the pump and the aspiration conduit 110. With such an apparatus, the signal from the pressure sensitive transducer 120 will cause the shut-off valve to be closed, thereby preventing the vacuum from increasing, but also holding the aspiration conduit at the level of vacuum reached before disconnection. A shut-off valve may also be necessary if a pump is used which cannot prevent backflow when it is shut off.

When the source of vacuum has been disconnected from the aspiration conduit 110, e.g., by stopping the pump 112, it is desirable to equalize the pressure in the irrigation and aspiration lines as soon as possible in order to release the blockage. When the pressures are so equalized, any suction force holding a tissue fragment against the aspiration inlet of the ultrasonic tool 52 is removed, and the tissue fragment can be easily dislodged. In the apparatus of this invention the pressure equalization is accomplished by means of pressure equalizing conduit 130, which conducts fluid from the source of irrigation fluid 102 to the aspiration conduit 110. Valve 132 in pressure equalizing conduit 130 controls the flow of fluid through conduit 130. Valve 132 is normally closed when the apparatus is being used to aspirate fluid and tissue from a surgical site. When a blockage occurs in the aspiration conduit 110, e.g., when a tissue fragment occludes the axial bore in the ultrasonic tool 52, the increased suction in the aspiration line 110 will be sensed by the pressure-sensitive transducer 120 which will in turn send a signal which shuts off the pump 112. Thereupon, the surgeon can release the vacuum in the aspiration conduit 110 by opening the valve 132 to admit irrigation fluid from the source of irrigation fluid 102 to the aspiration fluid conduit 110 via a pressure equalizing conduit 130 which is connected to the aspiration conduit 110 through the special fitting 140. Since the entire system is filled with liquid, the pressure equalization is very rapid, more rapid than in systems which adjust pressure by admitting air to the system. As soon as the pressure has been equalized, the transducer 120 will detect the lower level of suction and restart the pump. However, as long as valve 132 is open fluid will flow directly from the source of irrigation fluid 102 to aspiration conduit 110 and no substantial amount of suction will be applied to the surgical site through the aspiration conduit. When the valve 132 is closed the pump 112 will again draw fluid from conduit 110 and suction will thereby be reapplied to the surgical site.

It is greatly preferred that valve 132 be a remotely controlled valve, for example an electrically controlled valve actuated by a solenoid indicated schematically as 134. The solenoid 134 is energized by a source of electrical power under control of a switch operated by the surgeon. Preferably the switch is a foot switch so that the surgeon can easily equalize the pressure and dislodge occluding tissue without having to remove his hands from performing the surgical procedure. A check valve 109 is provided in irrigation supply tube 56 to prevent a backward surge of fluid in the irrigation supply tub 56 when valve 132 is opened to permit irrigation fluid to flow into the aspiration conduit.

Figure 2:
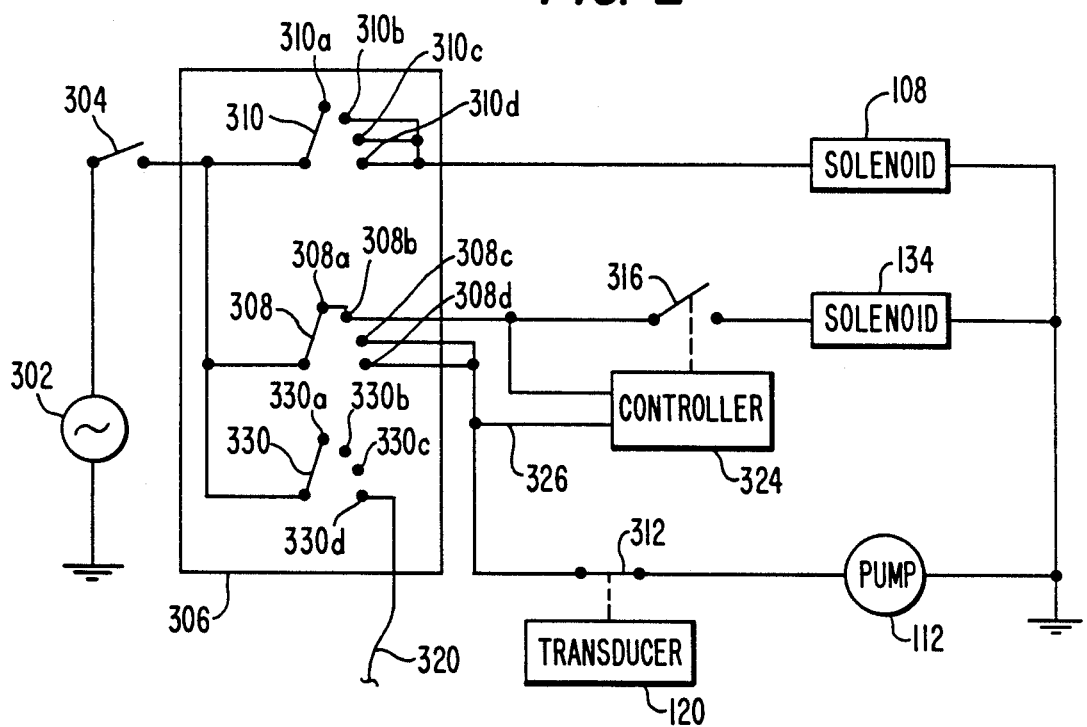
FIG. 2 illustrates an electrical control system for operating the fluid control system of the invention.

A schematic electrical circuit which can be used to control the flow control system of the invention is illustrated in FIG. 2. A source of electrical energy 302, e.g., conventional line current, is supplied to operate the electrical controls of the apparatus. Master switch 304 turns on the apparatus and supplies power to footswitch 306, having four positions, designated as positions zero through three. The foot switch 306 is provided with at least three movable contacts 308 and 310 each having an off position 308a and 310a respectively, corresponding to position 0 of the footswitch, and each movable contact engaging stationary contacts 308b-d, 310b-d corresponding to positions 1-3, respectively, of the footswitch. The footswitch is biased so that when no foot pressure is exerted thereon the switch is in position 0, the position shown, wherein contacts 308, 310 are in off positions 308a, 310a and and no power is connected to the control circuitry. Accordingly, solenoids 108 and 134 are not energized and valves 106 and 132 are closed to prevent irrigation fluid flow. When the footswitch 306 is depressed to position 1, contacts 308b and 310b are energized. Accordingly, solenoid 108 is energized to open valve 106 to supply irrigation fluid to the surgical handpiece 50. However, solenoid 134 is not energized because switch 316 is in its normally open position, and therefore valve 132 remains closed. Pump 112 is deactivated in footswitch position 1. When footswitch 306 is further depressed to position 2, contacts 308c and 310c are energized. Solenoid 108 remains energized, and accordingly, valve 106 remains open to supply irrigation fluid. Solenoid 134 is disconnected, and therefore valve 132 cannot open when the footswitch is in this position. Pump 112 is energized via normally closed switch 312 which is under the control of pressure transducer 120. This control may be mechanical or electrical as is well known to those skilled in the art. Accordingly, pump action fills aspiration conduit 110 with irrigation fluid. Switch 312 will be normally closed when the suction in the aspiration conduit 110 does not exceed a predetermined value, and will open when that value is exceeded. At the start of the surgical procedure, footswitch 306 will be depressed to position 3 to energize the ultrasonic surgical tool via wire 320 leading to the ultrasonic generator and control circuits for the handpiece which are entirely conventional and are not shown. The surgeon now proceeds with ultrasonic cutting using the tool 52 in handpiece 50. During the normal course of the surgical procedure, the switch 312 will be closed so that the pump 112 provides a source of suction for aspirating fluid and fragmented tissue from the surgical site, while irrigation fluid is supplied through open valve 106. The pressure equalizing conduit 130 remains closed normally. When an occlusion occurs, the vacuum is aspiration conduit 110 increases and pressure-sensitive transducer 120 causes switch 312 to open, shutting off pump 312. The surgeon will ordinarily be alerted to the occurrence of a blockage when the sound of the operating pump motor stops. He may, of course, also observe it through his operating microscope, or a special alarm, also operated by the pressure-sensitive transducer, may be provided. The surgeon thereupon can equalize the pressure by raising his foot, and moving footswitch 306 from position 3 to position 1, thus allowing the footswitch contacts to return to the position wherein contacts 308b and 310b are energized. When the footswitch 306 makes the transition from position 2 to position 1 triggered controller 324, which controls switch 316, is activated and momentarily opens switch 316. Triggered controller 324 receives power via contact 308b of the switch 306 and may include a conventional single-pulse circuit, e.g., a one-shot multivibrator, which supplies a single pulse to an actuator, e.g., a relay coil, which momentarily closes switch 316. The single-pulse circuit may be triggered via connection 326 when the footswitch 306 moves from position 2 to position 1. The triggered controller 324 and its circuitry are conventional and readily implemented by one skilled in the art. Solenoid 134 is thus momentarily actuated by switch 316 to open valve 132 in pressure equalizing conduit 130 to admit irrigation fluid directly from the source of irrigation fluid 102 into the aspiration conduit 110 to relive the suction in conduit 110. With the removal of the suction in aspiration conduit 110, no suction force holds tissue fragments at the entrance of the axial bore in the ultrasonic tool 52, and the fragments may easily be dislodged. The surgeon may then continue the procedure by depressing the foot switch to positions 2 and 3. Valve 132 is by this time closed and suction is restored to the aspiration conduit 110. While the described control system represents one circuit which accomplishes the objects of the invention, it will be recognized that alternate circuits may be employed.

Figure 3:
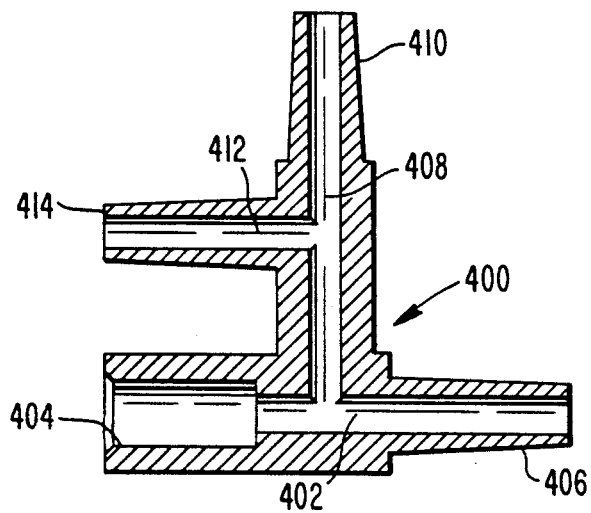
FIG. 3 illustrates a fluid connecting fitting specially adapted for connecting aspiration conduit, pressure relief conduit and pressure sensing conduit in the surgical irrigation-aspiration system of this invention.

The invention also encompasses a special fitting 400 shown in cross section in FIG. 3. This connecting fitting is specially adapted to fulfill the function of connecting together the aspiration conduit, the pressure relief conduit and the pressure-sensitive transducer. The fitting comprises a first rigid tubular fluid conduit 402 having a female connecting member 404 at one end for receiving the aspiration tubing 110 coming from the handpiece 52. This tubing carries aspirated fluid together with fragmented tissue, and the female connection provides a smooth internal wall for the conduit in order to reduce the chance of clogging. The tubular conduit 402 is provided at its other end with a male connecting member 406 for connecting to the tubing 113 leading to the source of suction, e.g., pump 112. A second rigid tubular fluid conduit 408, in fluid communication with the first tubular conduit 402 between the end connecting members 404 and 406, is arranged generally at right angles to the first conduit 402. The second fluid conduit 408 has a male tapered connecting member 410 at its free end adapted to mate with a female tapered connecting fitting on the filter housing 126 or with the tubing 122 leading to the pressure-sensitive transducer 120. A third rigid fluid conduit 412 has one end connected to and in fluid communication with the second fluid conduit 408 at a point intermediate between its ends. The other end 414 of the third tubular conduit 412 is tapered to receive the end of the pressure equalizing conduit 130. The third fluid conduit 412 is arranged generally at right angles to the second tubular conduit 408 and parallel to the first tubular conduit 402. This special connecting fitting 400 permits the rapid and convenient connection of all the fluid conducting members associated with the pressure equalizing function of the apparatus of this invention.

the invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A fluid control apparatus for use with a surgical irrigation and aspiration instrument adapted for irrigation and aspiration of a surgical site located in a small elastic chamber, said fluid control apparatus comprising:
   a source of irrigation fluid,
   an irrigation fluid conduit means for conducting irrigation fluid from said source of irrigation fluid to the surgical site,
   an aspiration fluid conduit means for removing fluid from the surgical site,
   a controllable pump means in fluid communication with said aspiration fluid conduit means for providing suction in said aspiration fluid conduit means,
   a pressure sensitive transducer means in fluid communication with said aspiration fluid conduit means for sensing a pressure in said aspiration fluid conduit means and generating a control signal for said pump means,
   a pressure relief fluid conduit means connecting said source of irrigation fluid to said aspiration fluid conduit means for providing fluid communication between said source of irrigation fluid and said aspiration fluid conduit means,
   a controllable valve means for controlling the fluid flow in said fluid pressure relief fluid conduit means, and
   a control means for controlling said controllable valve means.

2. The apparatus of claim 1 wherein said controllable valve means is an electrically-controllable valve.

3. The apparatus of claim 2 wherein said control means for said electrically-controllable valve is an electrical switch.

4. The apparatus of claim 3 wherein said electrical switch is a foot-actuated switch.

5. The apparatus of claim 1 wherein said pump means is a peristaltic pump.

6. The apparatus of claim 1 further comprising a check valve means for preventing fluid backflow in said irrigation fluid conduit means.

7. The apparatus of claim 1 further comprising a shut-off valve means in said irrigation fluid conduit means.

8. The apparatus of claim 1 further comprising a check valve means positioned in said irrigation fluid conduit means for preventing the backflow of fluid in said irrigation fluid conduit means towards said source of irrigation fluid into said aspiration fluid conduit means.

9. The apparatus of claim 8 further comprising a control valve positioned in said irrigation fluid conduit means between said source of irrigation fluid and said check valve means.

10. The apparatus of claim 9 wherein said control valve is a shut-off valve.

11. The apparatus of claim 9 wherein said control valve is operated by a solenoid.

12. The apparatus of claim 1 wherein said pressure relief fluid conduit means is directly connected to said irrigation fluid conduit means for supplying irrigation fluid to said aspiration fluid conduit means as needed.

13. A fluid control apparatus for use with a surgical irrigation and aspiration instrument adapted for irrigation and aspiration of a surgical site located in a small elastic chamber, said fluid control apparatus including an aspiration fluid conduit for conducting fluid away from the surgical site, a suction pump for providing suction in said aspiration fluid conduit, a pressure relief fluid conduit for releasing fluid into said aspiration fluid conduit, and a transducer in fluid communication with said aspiration fluid conduit and operatively connected to said suction pump, wherein the improvement comprises a connection fitting comprising:

a first tubular fluid conduit having a fluid connection at a first end connectable to said suction pump and a fluid connection fitting at a second end connectable to said aspiration fluid conduit, a second tubular fluid conduit having one end in fluid communication with said first tubular fluid conduit, and another end connectable to said pressure relief fluid conduit, said second tubular fluid conduit being arranged substantially at right angles to said first tubular fluid conduit, a third tubular fluid conduit having one end in fluid communication with said second tubular fluid conduit, and another end connectable to said pressure relief fluid conduit, and said third tubular fluid conduit being arranged generally at right angles to said second tubular fluid conduit and generally parallel to said first tubular fluid conduit.

14. The apparatus of claim 13 wherein said fluid connection at said first end is a male fluid connection fitting.

15. The apparatus of claim 14 wherein said fluid connection at said second end is a female fluid connection fitting.

16. The apparatus of claim 13 wherein said another end of said second tubular fluid conduit is a male fluid connection fitting.

17. The apparatus of claim 13 wherein said another end of said third tubular fluid conduit is a male fluid connection fitting.

18. The apparatus of claim 13 wherein said second fluid connection at said second end is a female fluid connection fitting.

19. The apparatus of claim 18 wherein said female fluid connection fitting defines a smooth internal conduit wall to reduce the chance of clogging with aspirated fragmented tissue.

20. The apparatus of claim 13 wherein said first tubular fluid conduit comprises a first rigid tubular fluid conduit, said second tubular fluid conduit comprises a second rigid tubular fluid conduit, and said third tubular fluid conduit comprises a third rigid tubular fluid conduit.

21. A fluid control apparatus for use with a surgical irrigation and aspiration instrument adapted for irrigation and aspiration of a surgical site located in a small elastic chamber, said fluid control apparatus comprising:

an irrigation fluid conduit mans for conducting irrigation liquid from a source of irrigation liquid to the surgical site, an aspiration fluid conduit means for removing fluid from the surgical site, a suction means in fluid communication with said aspiration fluid conduit means for providing suction in said aspiration fluid conduit means, a liquid pressure equalizing means for admitting irrigation liquid from the source of irrigation liquid to said aspiration fluid conduit means when a blockage occurs therein to vent the vacuum therein, and a preventing means for preventing at least some of the irrigation liquid from flowing in said irrigation fluid conduit means generally away from the surgical site when said liquid pressure equalizing means is admitting the irrigation liquid into said aspiration fluid conduit means.

22. The apparatus of claim 21 wherein said preventing means comprises a check valve operatively positioned in said irrigation fluid conduit means.

23. The apparatus of claim 22 wherein said check valve is operatively positioned between the surgical site, and the connection of said liquid pressure equalizing means and said irrigation fluid conduit means, and said check valve prevents irrigation liquid from flowing from the surgical site to said connection.

24. A fluid controlled apparatus for use with a surgical irrigation and aspiration instrument adapted for irrigation and aspiration of a surgical site located in a small elastic chamber, said fluid control apparatus comprising:

an irrigation fluid conduit means for conducting irrigation fluid from a source of irrigation fluid to the surgical site, an aspiration fluid conduit means for removing fluid from the surgical site, a pump means for providing suction in said aspiration fluid conduit means, and a transducer releasing means for releasing the pressure in said aspiration fluid conduit means to equilibrium, at the first indication of an occlusion of said aspiration fluid conduit means, by causing the introduction of venting liquid having the same pressure as that of the irrigation fluid in said irrigation fluid conduit means into said aspiration fluid conduit means.

25. The apparatus of claim 24 wherein said releasing means includes a transducer in communication with said aspiration fluid conduit means and operatively associated with said pump means, and a bacteria-retentive filter means for filtering the fluid flowing to said transducer.

26. The apparatus of claim 24 wherein said releasing means stops the vacuum effect of said pump means on said aspiration fluid conduit means at said first indication.

27. The apparatus of claim 24 wherein said releasing means includes a user operated and actuated switch means.

28. The apparatus of claim 27 wherein said releasing means includes a fluid conduit for providing fluid to said aspiration fluid conduit means, and a valve in said fluid conduit for controlling the flow of fluid from said fluid conduit into said aspiration fluid conduit means, and said switch means being operatively connected to said valve for opening said valve when the occlusion is detected.

29. For a fluid control apparatus for use with a surgical irrigation and aspiration instrument adapted for irrigation and aspiration of a surgical site located in a small elastic chamber, the fluid control apparatus including an aspiration fluid conduit for conducting fluid away from the surgical site, a suction pump for providing suction in the aspiration fluid conduit, a pressure relief fluid conduit for releasing fluid into the aspiration fluid conduit, and a transducer in fluid communication with the aspiration fluid conduit and operatively connected to the suction pump, a connection fitting comprising:
- a first tubular fluid conduit having a fluid connection at a first end operatively connectable to the suction pump and a fluid connection fitting at a second end operatively connectable to the aspiration fluid conduit,
- a second tubular fluid conduit having one end in fluid communication with said first tubular fluid conduit, and another end operatively connectable to the pressure relief fluid conduit,
- said second tubular fluid conduit being arranged substantially at right angles to said first tubular fluid conduit,
- a third tubular fluid conduit having one end in fluid communication with said second tubular fluid conduit, and another end operatively connectable to the pressure relief fluid conduit, and
- said third tubular fluid conduit being arranged generally at right angles to said second tubular fluid conduit and generally parallel to said first tubular fluid conduit, 30. The connection fitting of claim 27 wherein said fluid connection at said first end is a male fluid connection fitting.

31. The connection fitting of claim 30 wherein said fluid connection at said second end is a female fluid connection fitting.

32. The connection fitting of claim 29 wherein said another end of said second tubular fluid conduit is a male fluid connection fitting.

33. The connection fitting of claim 29 wherein said another end of said third tubular fluid conduit is a male fluid connection fitting.

34. The connection fitting of claim 29 wherein said second fluid connection at said second end is a female fluid connection fluid.

35. The connection fitting of claim 29 wherein said first tubular fluid conduit comprises a first rigid tubular fluid conduit, said second tubular fluid conduit comprises a second rigid tubular fluid conduit, and said third tubular fluid conduit comprises a third rigid tubular fluid conduit.

36. A fluid controlled apparatus for use with a surgical irrigation and aspiration instrument adapted for irrigation and aspiration of a surgical site located in a small elastic chamber, said fluid control apparatus comprising:
- an irrigation fluid conduit means for conducting irrigation fluid from a source of irrigation fluid to the surgical site,
- an aspiration fluid conduit means for removing fluid from the surgical site,
- a pump means for providing suction in said aspiration fluid conduit means,
- a releasing means for releasing the pressure in said aspiration fluid conduit means to equilibruim, at the first indication of an occlusion of said aspiration fluid conduit means, by using a venting liquid having the same pressure as that of the irrigation fluid in said irrigation fluid conduit means, and
- said releasing means including a transducer in communication with said aspiration fluid conduit means and operatively associated with said pump means, and a bacteria-retentive filter means for filtering the fluid flowing to said transducer.

37. The apparatus of claim 36 wherein said releasing means stops the vacuum effect of said pump means on said aspiration fluid conduit means at said first indication.

38. The apparatus of claim 36 wherein said releasing means includes a user operated and actuated switch means.

39. The apparatus of claim 38 wherein said releasing means includes a fluid conduit for providing fluid to said aspiration fluid conduit means, and a valve in said fluid conduit for controlling the flow of fluid from said fluid conduit into said aspiration fluid conduit means, and said switch means is operatively connected to said valve for opening said valve when the occlusion is detected.

40. A fluid control apparatus for use with a surgical irrigation and aspiration instrument adapted for irrigation and aspiration of a surgical site located in a small elastic chamber, said fluid control apparatus comprising:
- an irrigation fluid conduit for conducting irrigation fluid from a source of irrigation fluid to the surgical site,
- an aspiration fluid conduit means for removing fluid from the surgical site,
- a suction means in fluid communication with said aspiration fluid conduit mans for providing suction in said aspiration fluid conduit means,
- a liquid pressure equalizing means for admitting irrigation liquid from the source of irrigation fluid to said aspiration fluid conduit means when a blockage occurs therein to vent the vacuum therein,
- said liquid pressure equalizing means includes a pressure equalizing conduit providing communication for the irrigation fluid from said irrigation fluid conduit means to said aspiration fluid conduit means,
- said pressure equalizing conduit connects directly to said irrigation fluid conduit means so that the irrigation liquid can flow through at least a portion of said irrigation fluid conduit means to said aspiration fluid conduit means.

41. The apparatus of claim 40 further comprising a check valve means operatively connected to said irrigation fluid conduit means at a location between the connection of said pressure equalizing conduit and said irrigation fluid conduit means, and the surgical site for preventing at least some of the irrigation liquid from flowing in said irrigation fluid conduit means towards the source of irrigation liquid when said liquid pressure equalizing means is admitting the irrigation liquid into said aspiration fluid conduit means.

42. A fluid control apparatus for use with a surgical irrigation and aspiration instrument adapted for irrigation and aspiration of a surgical site located in a small elastic chamber, said fluid control apparatus comprising:
- an irrigation fluid conduit means for conducting irrigation fluid from a source of irrigation fluid to the surgical site,
- an aspiration fluid conduit means for removing fluid from the surgical site,
- a controllable pump means in fluid communication with said aspiration fluid conduit for providing suction in said aspiration fluid conduit means,
- a pressure sensitive transducer means communicating with said aspiration fluid conduit means for generating a pump control signal for said controllable pump means proportional to the vacuum in said aspiration fluid conduit induced by said pump means, said transducer senses a vacuum rise in said aspiration fluid conduit means, and said pump control signal causes said controllable pump means to quickly shut off when the vacuum in said aspiration fluid conduit means exceeds a predetermined value.

* * * * *

UNITED STATES PATENT AND TRADEMARK OFFICE
CERTIFICATE OF CORRECTION

PATENT NO. : 4,832,685
DATED : May 23, 1989
INVENTOR(S) : Stephen W. Haines

It is certified that error appears in the above-identified patent and that said Letters Patent are hereby corrected as shown below:

Column 9, Lines 19 and 20, the portion of claim 13 reading "pressure relief fluid conduit" should read --pressure-sensitive transducer--.

Column 11, Line 13, the portion of claim 29 reading "pressure relief fluid conduit" should read --pressure-sensitive transducer--.

Signed and Sealed this

Twenty-first Day of September, 1999

Attest:

Q. TODD DICKINSON

*Attesting Officer*     Acting Commissioner of Patents and Trademarks

(12) EX PARTE REEXAMINATION CERTIFICATE (5775th)
United States Patent
Haines

(10) Number: US 4,832,685 C1
(45) Certificate Issued: Jun. 12, 2007

(54) FLUID FLOW CONTROL SYSTEM AND CONNECTING FITTING THEREFOR

(75) Inventor: Stephen W. Haines, Santa Ana, CA (US)

(73) Assignee: Nestle S.A., Alcon Laboratories, Inc., Fort Worth, TX (US)

Reexamination Request:
No. 90/007,404, Jan. 31, 2005
No. 90/007,505, Apr. 8, 2005

Reexamination Certificate for:
Patent No.: 4,832,685
Issued: May 23, 1989
Appl. No.: 07/105,978
Filed: Oct. 6, 1987

Certificate of Correction issued Sep. 21, 1999.

Related U.S. Application Data

(63) Continuation of application No. 06/865,360, filed on May 21, 1986, now abandoned, which is a continuation of application No. 06/741,565, filed on Jun. 5, 1985, now abandoned.

(51) Int. Cl.
*A61M 1/00* (2006.01)

(52) U.S. Cl. .......................................................... 604/30
(58) Field of Classification Search ..................... 604/30
See application file for complete search history.

(56) References Cited

U.S. PATENT DOCUMENTS

| | | | |
|---|---|---|---|
| 3,920,014 A | 11/1975 | Banko | |
| 4,019,514 A | 4/1977 | Banko | |
| 4,168,707 A | 9/1979 | Douvas | |
| 4,395,258 A | 7/1983 | Wang | |
| 4,411,652 A | 10/1983 | Kramer et al. | |
| 4,650,462 A * | 3/1987 | DeSatnick et al. | 604/30 |
| 4,935,005 A * | 6/1990 | Haines | 604/30 |

* cited by examiner

*Primary Examiner*—Beverly M. Flanagan

(57) ABSTRACT

A fluid flow control apparatus specially adapted for use with an ultrasonic surgical tool which provides for irrigation of a surgical site and for aspirating fluid from the site comprises a source of irrigation fluid, comprises an irrigation fluid conduit or conducting the irrigation fluid to a surgical site, an aspiration fluid conduit for conducting fluid away from the surgical site, a suction pump connected to the aspiration fluid conduit for aspirating fluid from the surgical site, a pressure-sensitive control system for removing the source of suction from the aspiration conduit when a predetermined value of suction is exceeded, and a valve for controllably admitting irrigation fluid into the aspiration fluid conduit. A check valve in the irrigation conduit prevents a reverse surge when the irrigation fluid is admitted to the aspiration conduit.

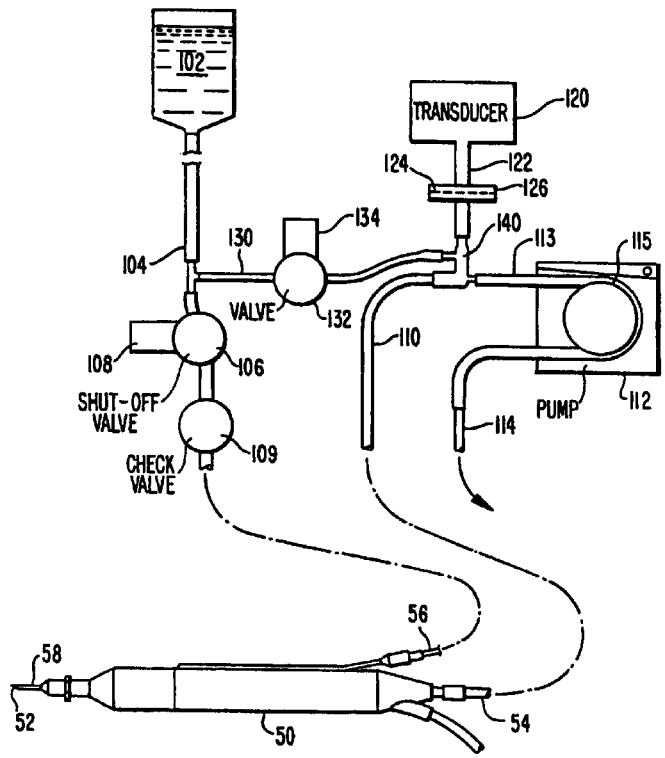

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 9-11, 13-20 and 29-35 is confirmed.

Claims 1-8, 12, 21-28 and 36-42 are cancelled.

\* \* \* \* \*